United States Patent
Cavagna et al.

(10) Patent No.: US 7,303,562 B2
(45) Date of Patent: Dec. 4, 2007

(54) PEDICLE SCREWS WITH INCLINED CHANNELS TO HOLD SUPPORT RODS

(75) Inventors: Remi Cavagna, Ploemeur (FR); Denis Huten, Vincennes (FR); Hugues Malandain, Southhaven, MS (US); Jose Gournay, Goele (FR)

(73) Assignee: SDGI Holdings, Inc., Wilmington, DE (US)

( * ) Notice: Subject to any disclaimer, the term of this patent is extended or adjusted under 35 U.S.C. 154(b) by 483 days.

(21) Appl. No.: 10/168,135

(22) PCT Filed: Dec. 22, 2000

(86) PCT No.: PCT/IB00/01956

§ 371 (c)(1),
(2), (4) Date: Jan. 31, 2003

(87) PCT Pub. No.: WO01/47425

PCT Pub. Date: Jul. 5, 2001

(65) Prior Publication Data

US 2003/0144664 A1  Jul. 31, 2003

(30) Foreign Application Priority Data

Dec. 24, 1999 (FR) .................................. 99 16492
May 3, 2000 (FR) .................................. 00 05655

(51) Int. Cl.
*A61B 17/58* (2006.01)
*A61F 2/30* (2006.01)

(52) U.S. Cl. ....................................................... 606/61

(58) Field of Classification Search .................. 606/61, 606/73, 60, 72
See application file for complete search history.

(56) References Cited

U.S. PATENT DOCUMENTS

| | | | | |
|---|---|---|---|---|
| 1,980,093 A | * | 11/1934 | Rosenberg | 411/412 |
| 4,760,843 A | * | 8/1988 | Fischer et al. | 606/73 |
| 5,005,562 A | * | 4/1991 | Cotrel | 606/61 |
| 5,067,955 A | | 11/1991 | Cotrel | |
| 5,127,912 A | | 7/1992 | Ray et al. | |

(Continued)

FOREIGN PATENT DOCUMENTS

EP  0 283 373 A1  9/1988

(Continued)

*Primary Examiner*—Anuradha Ramana
(74) *Attorney, Agent, or Firm*—Woodard, Emhardt, Moriarty, McNett & Henry LLP (57) ABSTRACT

This invention is a pedicle screw (1), comprising a threaded rod (2) having a longitudinal axis (XX) and a head (4) in which there is a channel (5) adapted to receive a spinal support rod, and a means for blocking the rod; the channel is formed such that its longitudinal axial plane (P) is inclined relative to the longitudinal axis (XX) of the threaded rod. The head (4) of the screw being made up of two flanks (6, 7), a threaded hole (11) is formed in one of them; the inclination of the channel (5) relative to the axis of the treaded rod (2) makes it possible to place a tool for blocking the rod in the channel without this tool coming into contact with the muscle tissues delimiting the incision. Moreover, the threaded seat (11) permits the positioning of instruments without obstructing the channel for passage of the rod.

36 Claims, 11 Drawing Sheets

U.S. PATENT DOCUMENTS

| | | | |
|---|---|---|---|
| 5,154,719 A * | 10/1992 | Cotrel | 606/73 |
| 5,176,679 A * | 1/1993 | Lin | 606/61 |
| 5,217,497 A * | 6/1993 | Mehdian | 606/61 |
| 5,282,863 A * | 2/1994 | Burton | 606/61 |
| 5,312,404 A * | 5/1994 | Asher et al. | 606/61 |
| 5,380,325 A * | 1/1995 | Lahille et al. | 606/61 |
| 5,382,248 A * | 1/1995 | Jacobson et al. | 606/60 |
| 5,387,212 A * | 2/1995 | Yuan et al. | 606/61 |
| 5,466,238 A | 11/1995 | Lin | |
| 5,544,993 A * | 8/1996 | Harle | 411/414 |
| 5,562,663 A * | 10/1996 | Wisnewski et al. | 606/61 |
| 5,603,714 A * | 2/1997 | Kaneda et al. | 606/61 |
| 5,669,911 A * | 9/1997 | Errico et al. | 606/61 |
| 5,868,051 A * | 2/1999 | Pakos | 82/110 |
| 5,941,885 A * | 8/1999 | Jackson | 606/104 |
| 6,030,162 A * | 2/2000 | Huebner | 411/413 |
| 6,074,393 A * | 6/2000 | Sitoto | 606/73 |
| 6,096,039 A * | 8/2000 | Stoltenberg et al. | 606/61 |
| 6,146,383 A * | 11/2000 | Studer et al. | 606/61 |
| 6,187,005 B1 * | 2/2001 | Brace et al. | 606/61 |
| 6,224,596 B1 * | 5/2001 | Jackson | 606/61 |
| 6,261,288 B1 * | 7/2001 | Jackson | 606/61 |
| 6,264,658 B1 * | 7/2001 | Lee et al. | 606/61 |
| 6,280,443 B1 * | 8/2001 | Gu et al. | 606/61 |
| 6,488,681 B2 * | 12/2002 | Martin et al. | 606/61 |
| 6,547,789 B1 * | 4/2003 | Ventre et al. | 606/61 |
| 6,709,434 B1 * | 3/2004 | Gournay et al. | 606/61 |

FOREIGN PATENT DOCUMENTS

| | | |
|---|---|---|
| EP | 0 392 927 A2 | 10/1990 |
| EP | 0 472 017 A1 | 2/1992 |
| FR | 2 719 759 A1 | 11/1995 |
| JP | 10052440 | 2/1998 |

* cited by examiner

PEDICLE SCREWS WITH INCLINED CHANNELS TO HOLD SUPPORT RODS

The present invention relates to bone screws with a thread adapted to be screwed into a bone, and a fixing means located the other end that is designed for attaching a spinal rod to the screw.

BACKGROUND OF THE INVENTION

In order to maintain bones in specified orientation relationship, there are various known techniques for screwing a bone-fixing screw into bones in various parts of the body, such as the spine, and combining rods with said implanted screw so that the rods will be positioned alongside the bones. The screws of the prior art are provided with a rod-fixing means. The rod-fixing means have an opening that is located either parallel to the axial direction of thread or on the side thereof, but these solutions have problems; inserted rods slip out of place with the parallel arrangement, while with the latter, operators have to insert a rod at right angles to the axis of the thread, which can prove to be a difficult procedure.

SUMMARY OF THE INVENTION

In one aspect, this invention is a bolt for connecting a vertebra to a longitudinal member with a mounting portion at one end portion of the bolt and a connector portion at a second end of the bolt. The connector portion has a channel that is adapted to receive a spinal support rod and the longitudinal axial plane of the channel is oblique to the longitudinal axis of the mounting portion of the bolt. A screw is then threadably engaged into the connector portion in a manner that the longitudinal axis of the screw is substantially parallel to the longitudinal axial plane of the channel in the connector portion.

In another aspect, the invention is an apparatus to support the spine. The apparatus has a longitudinal member with at least one flat planar face formed therein that extends over at least part of the length of the longitudinal member. The apparatus also has two bolts. At least one of the bolts has a mounting portion at one end of the bolt and a connector portion at a second end of the bolt. The connector portion has a channel therein that is adapted to receive the longitudinal member and the channel is oblique to the longitudinal axis of the mounting portion of the bolt. The bolt then also has a screw that threadably engages the connector portion of the bolt to hold the longitudinal member in place.

In yet another aspect, the invention is also bolt for connecting a vertebra to a longitudinal member with a mounting portion at one end portion of the bolt and a connector portion at a second end of the bolt. The connector portion has a channel that is adapted to receive a spinal support rod and the longitudinal axial plane of the channel is oblique to the longitudinal axis of the mounting portion of the bolt. A screw is then threadably engaged into the wall in the channel of the connector portion so as to press against a longitudinal member residing in the channel when the screw is axially displaced out from the wall.

In still another aspect of the invention, the invention is an apparatus to support the spine. The apparatus includes at least one support rod and at least two pedicle screws. The pedicle screws have a head disposed at a one end and male threads disposed at the other end. The head portion has a channel therein that is adapted to receive the support rod. The male threads have an outside diameter and a core with a core diameter. The core diameter remains substantially constant between the screws, while the external diameter of the threads increases from one screw to the next screw.

In the case of a screw, the longitudinal centre plane of the channel containing the longitudinal axis of the threaded rod, the channel extends along the axis of the threaded rod. As the latter is also necessarily inclined in relation to the margins of the incision of the spine so as to be able to be anchored in a pedicle, the instruments employed for positioning these screws come into contact with the flesh and tissues bordering the incision, during the screwing and the other operations on the screw.

Thus, an object of the invention is to make available a bone-anchoring member which is such that the instruments associated with it can be used without coming into contact with the tissues defining the margin of the incision.

According to the invention, the channel is formed such that its longitudinal axial plane is inclined relative to the longitudinal axis of the bone-anchoring member.

Another object of the invention is to provide a solution to the following problem. It has been found that support rods of relatively small diameter, for example 3 mm, give rise to a considerable percentage of breaks following a certain period of use on the patient. It is therefore desirable to increase the flexural strength of these rods, but without increasing their diameter. A solution to this problem would be to use a pair of rods instead of one. For a rod having a diameter of 3 mm, for example, a pair of rods thus combined is equal in terms of flexural strength to a rod having a diameter of 3.6 mm. However, such a solution considerably increases the size and the cost price of the instrumentation since it requires two rods instead of one.

The invention therefore aims to provide a satisfactory solution to this problem.

According to the invention, at least one longitudinal flat is formed on the support rod and extends over at least part of the length of the rod, in such a way that the latter has, in a longitudinal axial plane of the channel, a different flexural strength depending on whether its flat extends perpendicular or parallel to the said longitudinal axial plane of the channel.

Thus, depending on whether the rod is oriented with its flat parallel to the longitudinal axial plane of the channel or by contrast perpendicular to this plane, the flexural strength of this rod will be different. This strength is of course greater when the flat is parallel to the axial plane of the channel.

With such an arrangement it is therefore possible, when so required, to increase the flexural strength of the rod by providing it with one or two flats and by modifying its orientation. This affords the advantage of avoiding the use of two identical rods, thereby reducing the size of the instrumentation and its cost price.

According to one embodiment of the invention, the rod has two flats parallel to one another and diametrically opposite, the rod having parts of circular cross section between its flats.

Other particulars and advantages of the invention will become clear from the following description in which reference is made to the attached drawings which show a number of illustrative and nonlimiting embodiments.

DETAILED DESCRIPTION OF THE PREFERRED EMBODIMENTS

Figure 1:
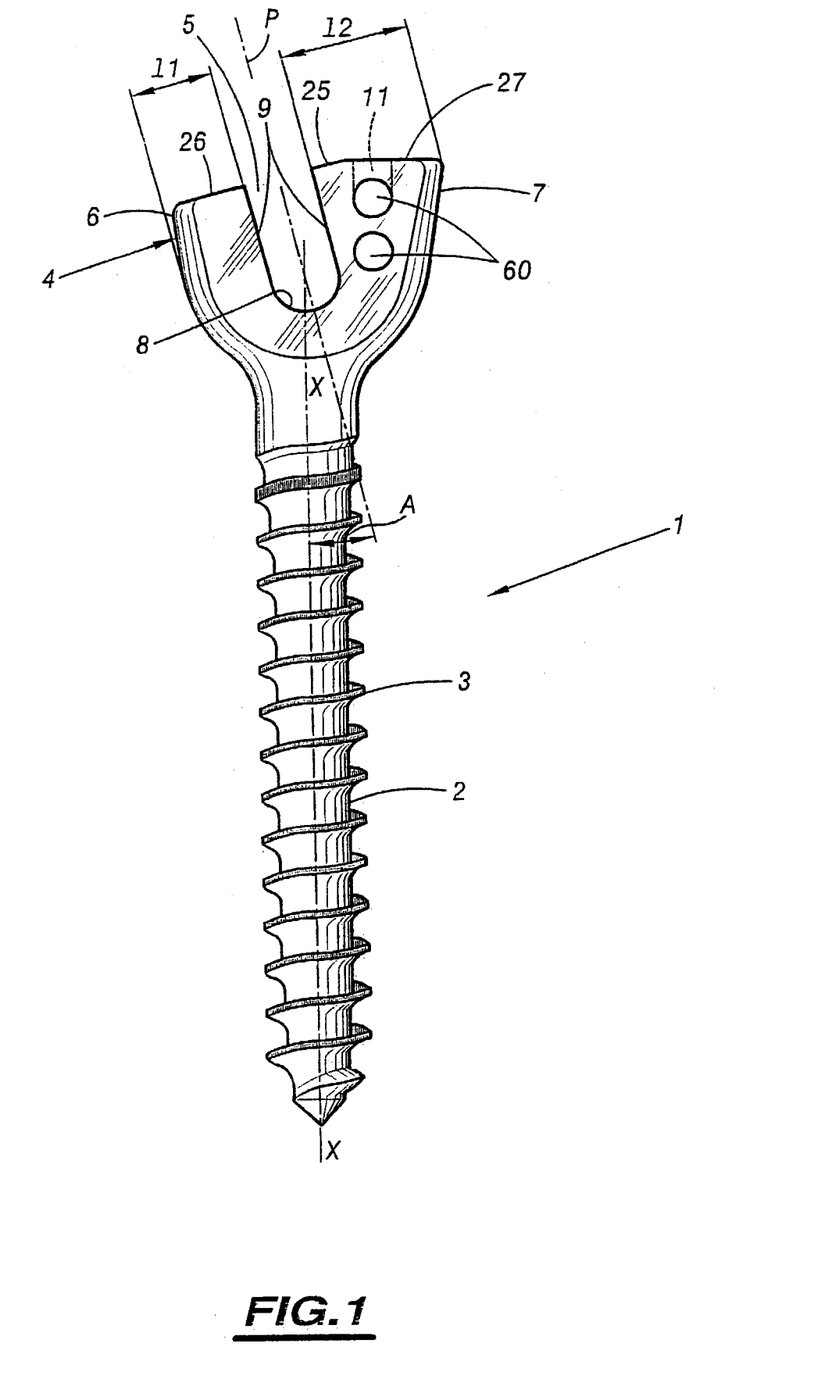
FIG. 1 is a front view, on an enlarged scale, of a pedicle screw according to the invention, intended for instrumentation for supporting the spine.
Figure 2:
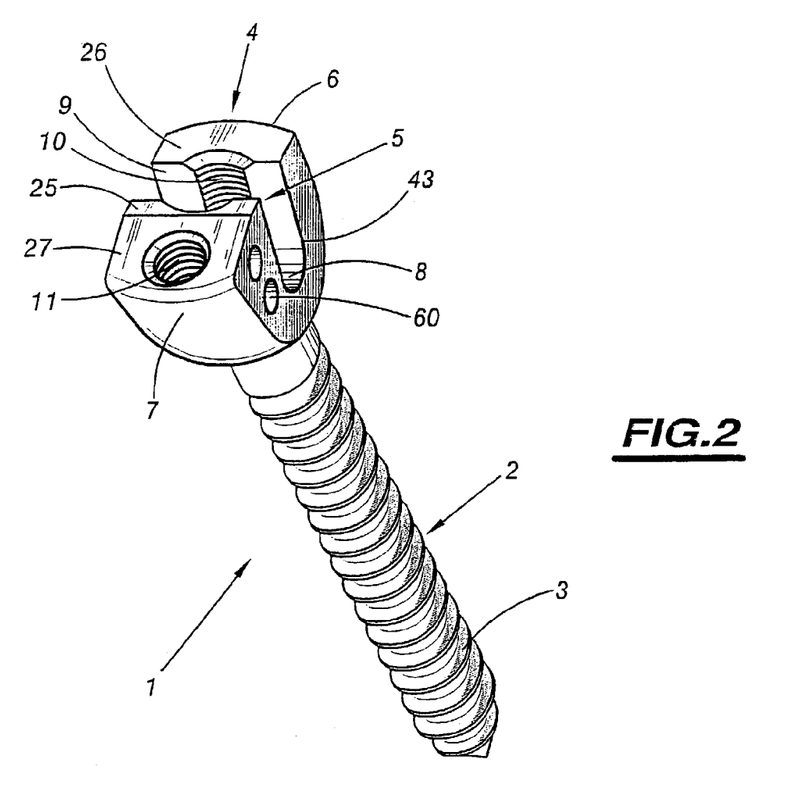
FIG. 2 is a perspective view, on an enlarged scale, of the pedicle screw in FIG. 1.
Figure 3:
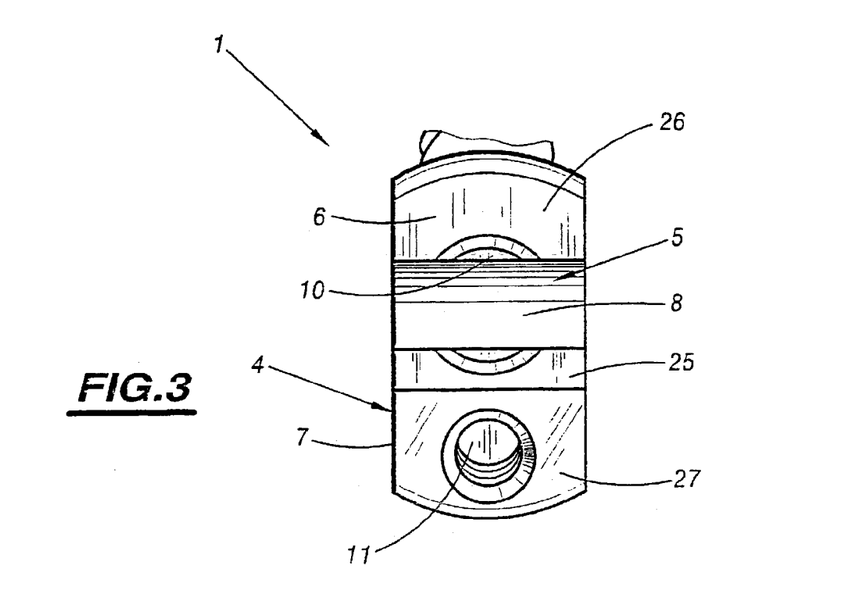
FIG. 3 is a top view of the head of the screw in FIGS. 1 and 2.

The pedicle screw 1 represented in FIGS. 1 to 3 is intended to form part of instrumentation for supporting the spine. This instrumentation has at least one support rod dimensioned to extend along at least two vertebrae and at least two pedicle screws for bone anchoring, such as pedicle screw 1.

Screw 1 has a threaded rod 2 provided with a bone thread 3 and a longitudinal axis X-X, and a head 4 in which there is a channel 5 having a U-shaped cross section and a longitudinal axial plane P. The channel 5, delimited by two flanks 6, 7 of the head 4, is adapted to receive a generally cylindrical support rod and for this purpose preferably has a bottom 8 of circular cross section. On its walls 9 there are threaded parts 10 intended to receive a screw (not shown) for blocking a support rod (not shown). This rod can be smooth or have a roughened surface or it can be the type of rod 36 which will be described below.

The U-shaped channel 5 is formed such that its longitudinal axial plane P is inclined by an angle A different from zero degrees relative to the longitudinal axis X-X of threaded rod 2. Thus, the rectilinear walls 9, which delimit either side of threaded parts 10 and channel 5 with its circular bottom 8, have an inclination A relative to the axis X-X.

This inclination A can have a value preferentially up to about 65 degrees (cf. FIG. 19-20) in either direction.

Figures 6, 7:
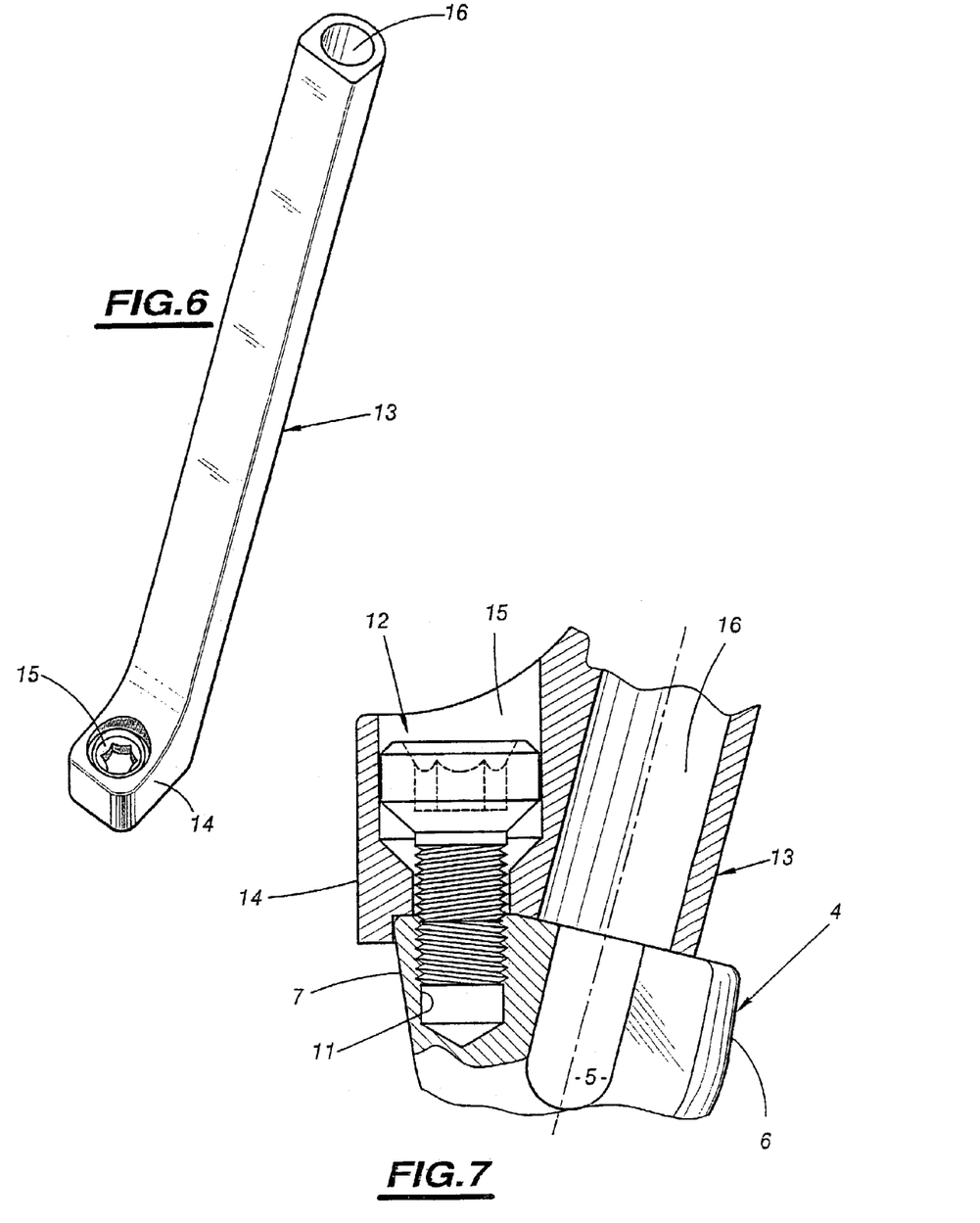
FIG. 6 is a perspective view of an instrument which can advantageously be used in combination with a screw according to the invention.
FIG. 7 is a partial longitudinal section, on an enlarged scale, of the head of a screw according to the invention and of the lower end of the instrument in FIG. 6, positioned on the head of the screw.

The flanks 6 and 7 delimiting the U-shaped channel 5 may have different respective widths 11, 12 in a direction perpendicular to the longitudinal axial plane P. In addition, a threaded hole 11 is formed in the flank 7 whose width 12 is the greater. This hole 11 is intended to receive a threaded member such as a screw 12 (FIG. 7) for fixing a piece to the screw 1, for example an instrument 13 (FIGS. 6-7).

Instrument 13 has a general tubular shape with an angled lower end 14 in which there is an orifice 15 for introducing the screw 12 into the threaded hole 11. Also arranged in the instrument 13 is an axial bore 16 which is open to each end of instrument 13, the angled end 14 being adapted to be applied on the end faces of the branches 6, 7 while the screw 12 can be screwed into the hole 11, in such a way that the bore 16 is coaxial with the threaded parts 10 (FIG. 3). The geometry of the head 4 of the screw 1 thus makes it possible to position the instrument 13 in such a way that a tool can be introduced axially into the bore 16, precisely and with ease into the axis of the channel 5, in order to easily carry out the screwing therein of a threaded plug for blocking the support rod passing through the channel 5.

Figure 4:
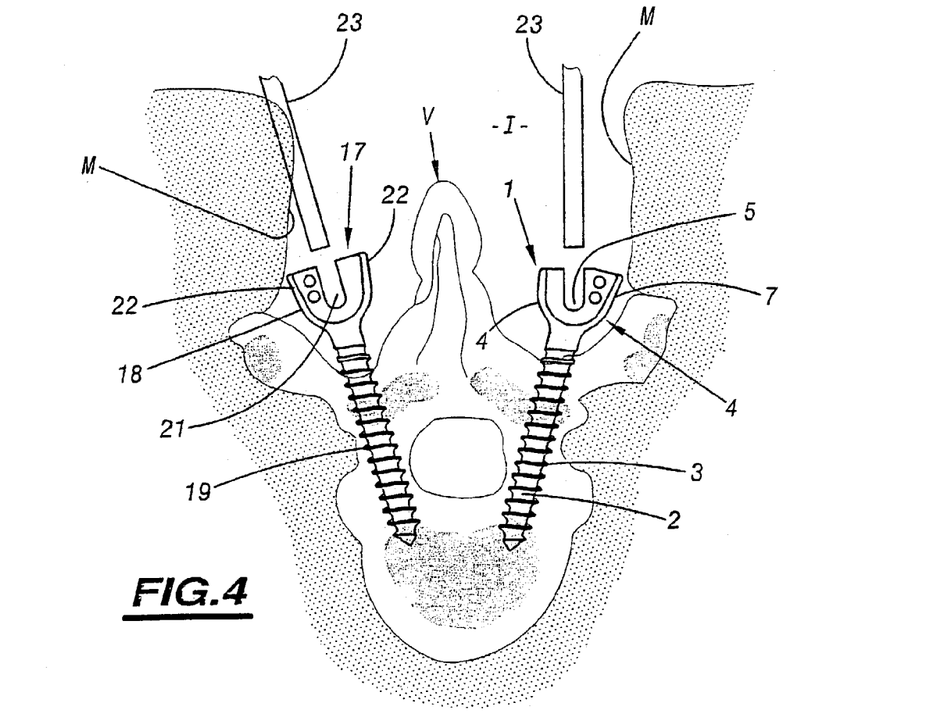
FIG. 4 is a view, in a horizontal plane, of two pedicle screws anchored in a vertebra, one of them according to the invention and the other according to the prior art.

FIG. 4 shows a screw 1, according to one embodiment of the invention, screwed into a pedicle of a vertebra V and also a screw 17, according to the prior art, screwed into the other pedicle of the same vertebra. To permit positioning of the screws, the surgeon has first made an incision I in the spine by the posterior approach, this incision I being delimited laterally by muscle tissues M. The screw 17 according to the prior art includes a head 18 which is integral with a threaded rod 19 and has a U-shaped channel 21 whose axial plane contains the longitudinal axis of the rod 19. The flanks 22 delimiting the channel 21 are thus similar in their dimensions and are symmetrical in relation to this axial plane and to the axis of the rod 19. As the screw 17 is also inclined in the pedicle in the direction of the adjacent tissues M, the result is that a tool 23 for screwing in the plug for blocking the support rod in the channel 21, necessarily placed in the axis of the channel 21, will interfere in an undesirable manner with the muscle tissues M.

By contrast, by virtue of the inclination of the channel 5 relative to the axis X-X of the screw 1 according to the invention, the screwing tool 23 can be introduced into the channel 5 without coming into contact with the tissues M.

Figure 5:
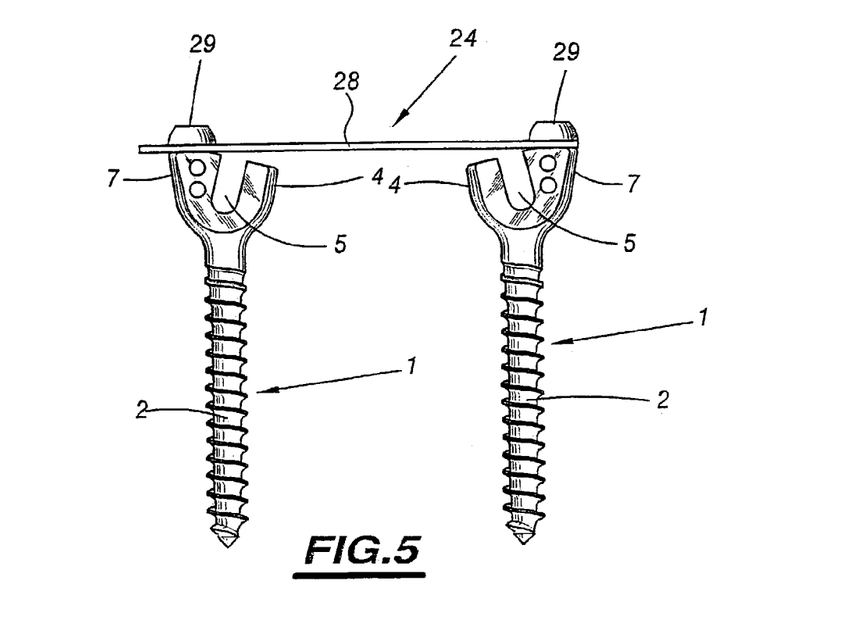
FIG. 5 is a front view of a pair of bone screws according to the invention, joined via a transverse connection device.

FIG. 5 illustrates the use of a transverse connection device 24 by virtue of the design of the wider flank 7 of the screw 1. The end face of this wide flank 7 is made up of a first plane part 25, situated in the plane of the plane face 26 forming the end of the flank 6, and of a second plane part 27 forming an obtuse angle with the plane part 25. (FIG. 1). The transverse connection device 24 is made up of a plate 28 whose ends bear on the plane part 27 of two screws 1, and of two members 29 for blocking the plate 28 on the screws 1. Each member 29 includes a threaded rod (not visible in FIG. 5) passing through a corresponding orifice of the plate 28 and being screwed into the associated threaded hole 11.

Figure 8:
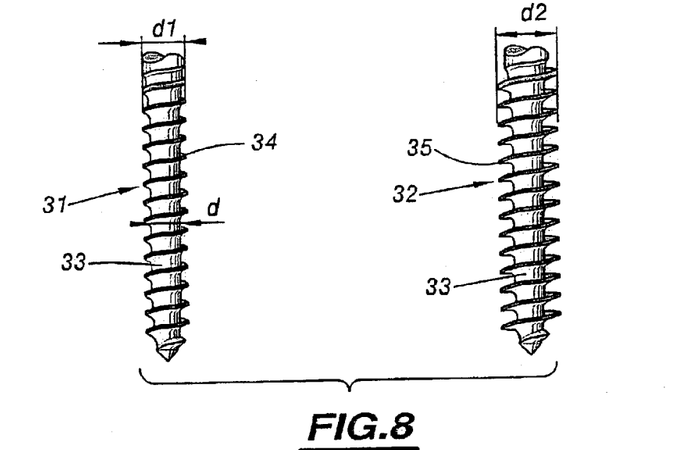
FIG. 8 is a partial front view of two bone screws which can be used in a spinal instrumentation according to the invention.

FIG. 8 shows two pedicle screws 31 and 32 for anchoring instrumentation for supporting the spine into bone. Each screw comprises a core 33 of diameter d, equipped with a respective thread 34 and 35, each also having an external diameter d1, d2, and a head (not shown). The diameter d of the core 33 is identical for both the screws 31, 32, while the external diameter of their respective threads 34, 35 increases from d1 to d2, for example from 5.5 to 7.5 mm. More generally, in the set of screws provided for by the invention, each screw such as 31, 32 comprises a cylindrical core 33 whose diameter is constant for all the screws, while the external diameters d1, d2 of their respective threads 34, 35 increase from one screw to the other, between defined limits. These screws can be of the conventional type, such as the screw 17 shown in FIG. 4, or can be according to the invention, such as the screw 1.

The identically rigid screws 31, 32 of this set do not have too great a diameter in relation to that of the support rods with which they may be associated. The diameter of the core 33 is of course chosen so that all the screws used in the spinal instrumentation in question have a sufficient mechanical strength, while the height of their thread varies from one screw to the other. In other words, the diameter of the core 33 of the screw remains identical from one screw to the other, irrespective of the external diameter of its thread.

Figure 9:
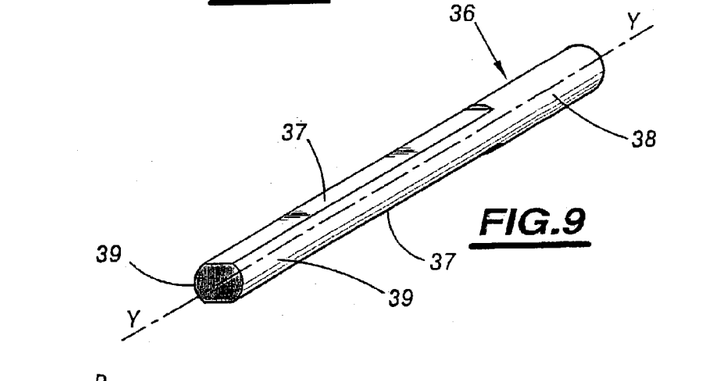
FIG. 9 is a perspective view of a support rod for spinal instrumentation, according to a third embodiment of the invention.
Figure 10:
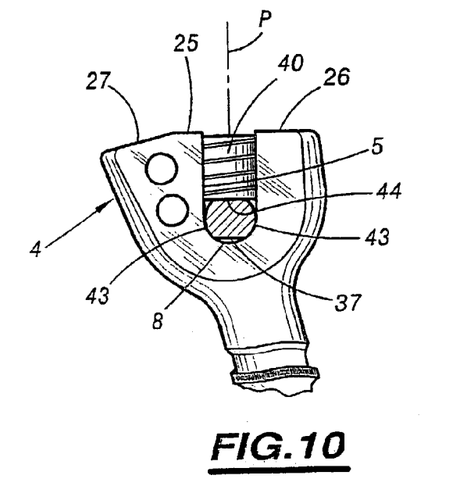
FIGS. 10 and 11 are front views in partial section showing the head of a screw according to FIGS. 1 to 3 associated with a support rod according to FIG. 9, arranged in a first orientation in FIG. 10 and in a second orientation in FIG. 11.
Figure 11:
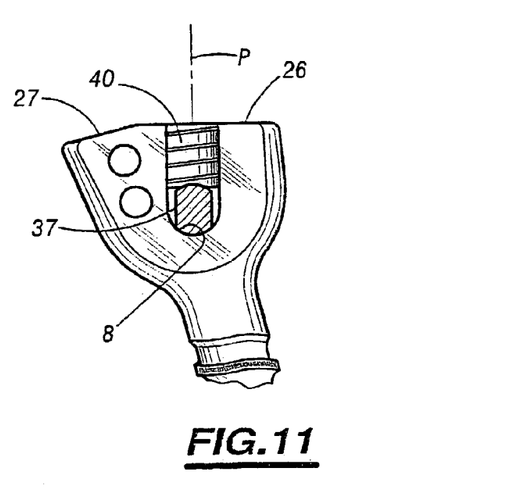

FIGS. 9 to 11 illustrate another embodiment of the invention in which a pedicle screw 1 is associated with a support rod 36 on which at least one longitudinal flat 37 is formed over at least part of the length of the rod 36, the remaining part 38 of which is cylindrical. In the example illustrated in FIGS. 9 to 11, two longitudinal flats 37 are arranged on the rod 36 and positioned diametrically opposite each other over part of the length of the rod. In addition, these flats 37 are identical, that is to say they are symmetrical with respect to the longitudinal axis Y-Y of the rod 37. For this reason, the latter has, in the longitudinal axial plane P of the channel 5 of the head 4, a different flexural strength depending on its orientation in this channel 5. More precisely, the flat or flats 37 can extend either perpendicular to the said axial longitudinal plane P of the channel 5 (FIG. 10) or parallel to it (FIG. 11). Between the flats 37, the rod 36 has two diametrically opposite parts 39 with contours of circular cross section.

The rounded bottom 8 of the channel 5 has a radius of curvature substantially equal to the radius of curvature of the circular parts 39. For this reason, when the rod 36 is positioned in such a way that its flats 37 are parallel to the axial plane P (FIG. 11), one of the circular contours 39 will bear on the circular bottom 8 by fitting it. Advantageously, the means for blocking the rod 36 in the channel 5, formed for example by a threaded plug 40, has a bearing face which comes into contact with the rod 36.

When the rod 36 is oriented with its flats 37 perpendicular to the axial plane P of the channel 5 (FIG. 10), its opposite circular contours 39 bear on rounded shoulders 43 which connect the bottom 8 to the plane walls of the channel 5 and whose radius of curvature is substantially equal to that of the circular contours 39. In this case, the plane end face of the plug 40 is applied tightly on one of the flats 37.

The arrangement of one or two flats such as 37 over at least part of the length of the support rod 36 thus makes it possible to vary its flexural strength in the axial plane P of the channel 5, depending on its orientation: when the flats 37 are perpendicular to the axial plane P (FIG. 10), its flexural strength in this plane is minimal, whereas when these flats 37 are placed parallel to the axial plane P (FIG. 11), its flexural strength is much greater. For this reason, the breaks which could occur hitherto with entirely cylindrical rods can be reduced by using a rod with a greater diameter and with a flat or flats, such as 36, suitably oriented in the channel 5.

The flat or flats make it possible to adapt the "stiffness" of the assembly to the pathology of the patient, by varying the orientation of the rod 37 (FIGS. 10 and 11).

By way of indicative and nonlimiting numerical example, for a rod having a diameter of 4 mm, the flats 37 can be separated by a distance of 3 mm. In a possible alternative, the flanks 6, 7 of the screw 1 can have equal widths. Similarly, the function of the threaded hole 11 can be provided by a threaded extension in the same location or by a geometry on the sides such as holes 60 or grooves 107 (FIGS. 19 and 22), making it possible to grip the screw via an instrument.

Figure 12:
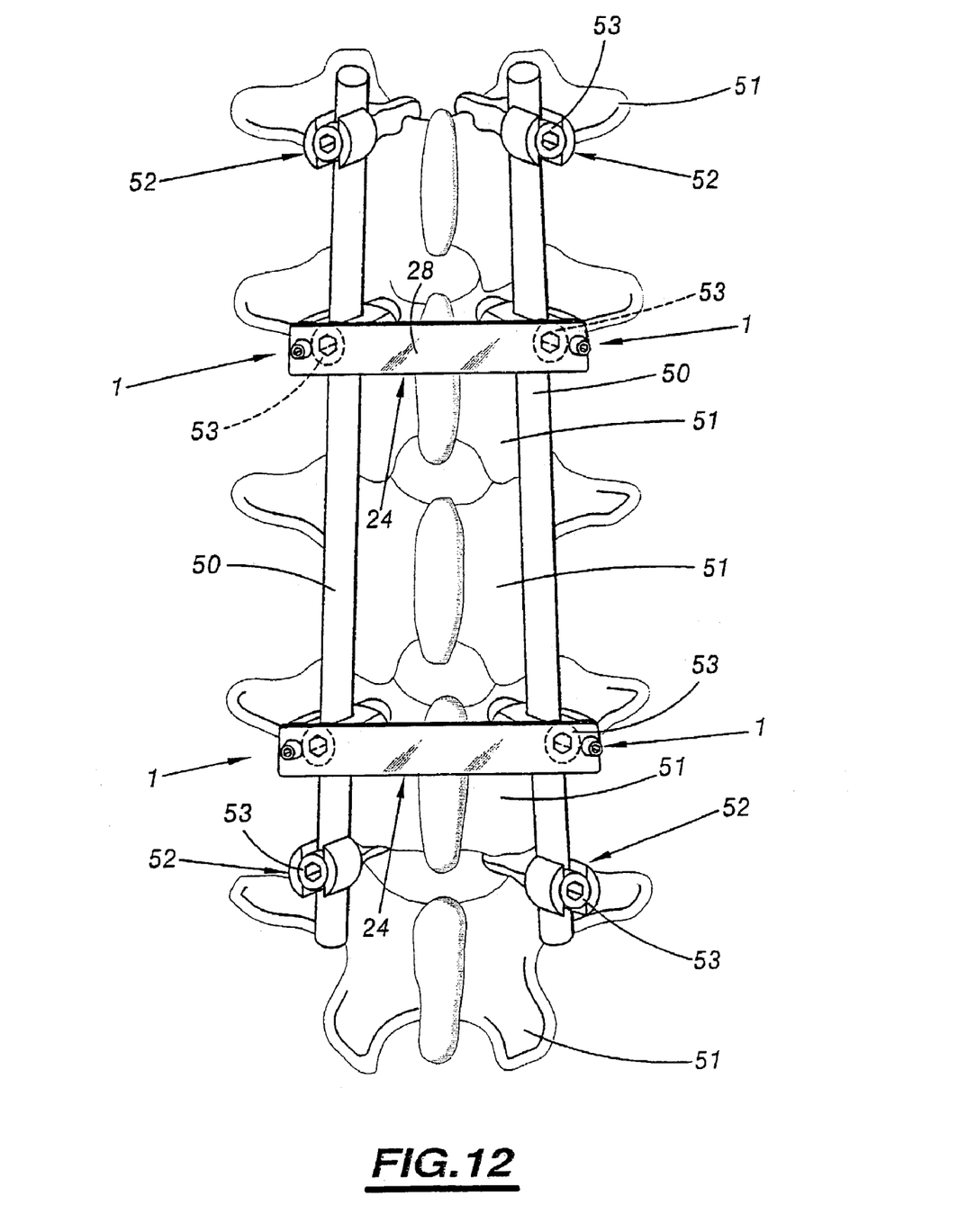
FIG. 12 is a front view of spinal osteosynthesis instrumentation according to the invention.

FIG. 12 illustrates instrumentation according to the invention used in conjunction with prior art screws 52, including two cylindrical vertebral rods 50 extending along a segment of the spine comprising four vertebrae 51. These rods are also equipped with pedicle screws 1, which are equipped with threaded plugs 53 for blocking the rods 50, and also, at the ends of the said rods, with bone-anchoring hooks 52 also provided with threaded plugs 53.

The pairs of screws 1 are connected by transverse connection devices 24.

Of course, the cylindrical rods 50 can be replaced by rods 36 with flats 37, and the plugs 53 can be replaced by plugs 40 or 41.

Figure 13:
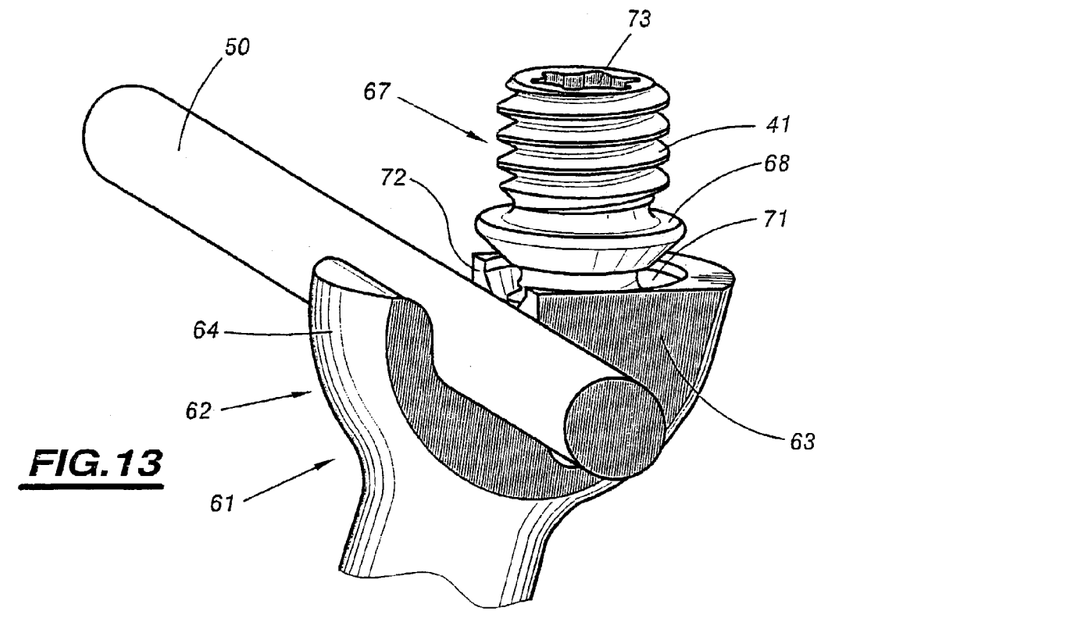
FIG. 13 is a partial perspective view, on an enlarged scale, of a second embodiment of the screw in FIGS. 1 to 3 and of its means for blocking the support rod.
Figure 14:
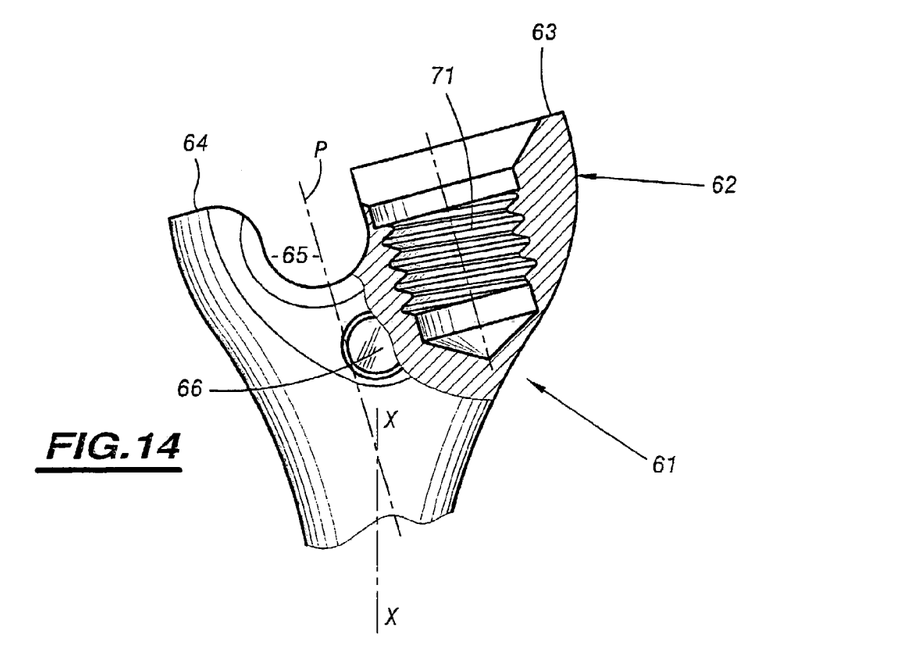
FIG. 14 is a partial side view of the screw in FIG. 13.
Figure 15:
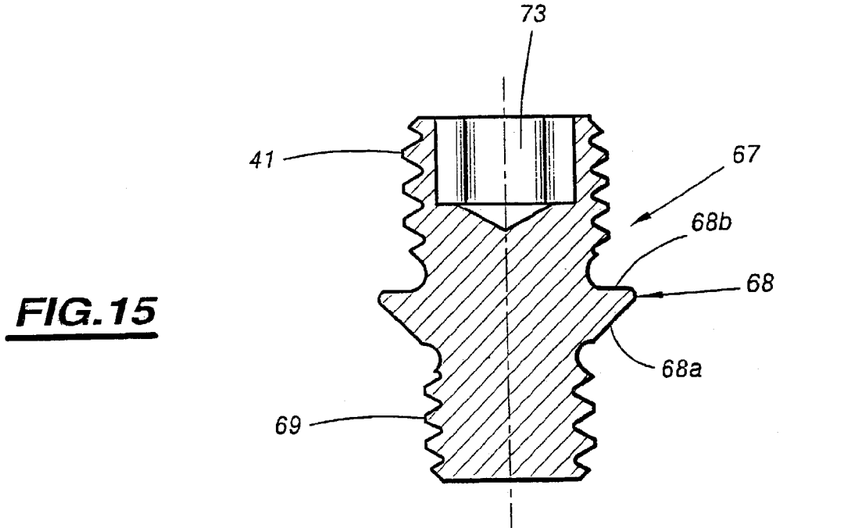
FIG. 15 is a longitudinal section of the means for blocking the rod associated with the screw in FIGS. 13 and 14.

FIGS. 13 to 15 illustrate a second embodiment of the screw in FIGS. 1 to 3. In this embodiment, the screw 61 includes a head 62 consisting of two flanks 63, 64 of unequal width and delimiting between them a channel 65 of U-shaped profile. Formed on one side of the body 62 there is also a hole 66 for gripping the screw via an instrument (not shown). The means for blocking the support rod 50 is a threaded plug 67 provided with a collar 68 which radially delimits two threaded parts 41 and 69. In one of the flanks delimiting the channel 65, namely in the wider flank 63, a threaded hole 71 is formed which has an interruption 72 on its part contiguous with the channel 65, so as to communicate laterally with the latter. In this way, after the plug 67 has been screwed into the hole 71, the collar 68 comes into blocking engagement on the rod 50 placed in the channel 65. The upper thread 41 projecting above the collar 68 can be joined to a transverse connection plate, such as 24 (FIG. 12), to which it is fixed by a nut (not shown).

Formed in the threaded plug 67 there is a profiled impression 73 for receiving a corresponding screwing tool (not shown). It will be noted that the collar 68 has an asymmetrical profile formed by a flank 68a, inclined in such a way as to be able to bear on the rod 50 at the end of screwing of the plug 67, and a second flank 68b extending radially, almost perpendicular to the longitudinal axis of the plug 67.

Figure 16:
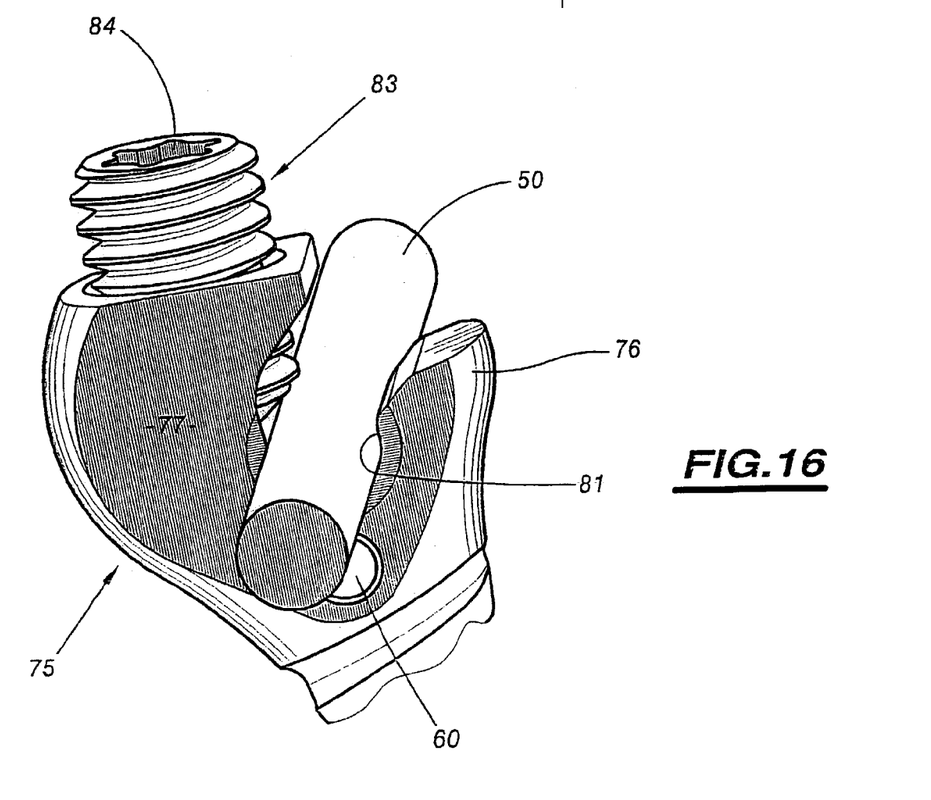
FIG. 16 is a partial perspective view, on an enlarged scale, of a third embodiment of the screw in FIGS. 1 to 3 and of its means for blocking the rod.
Figure 17:
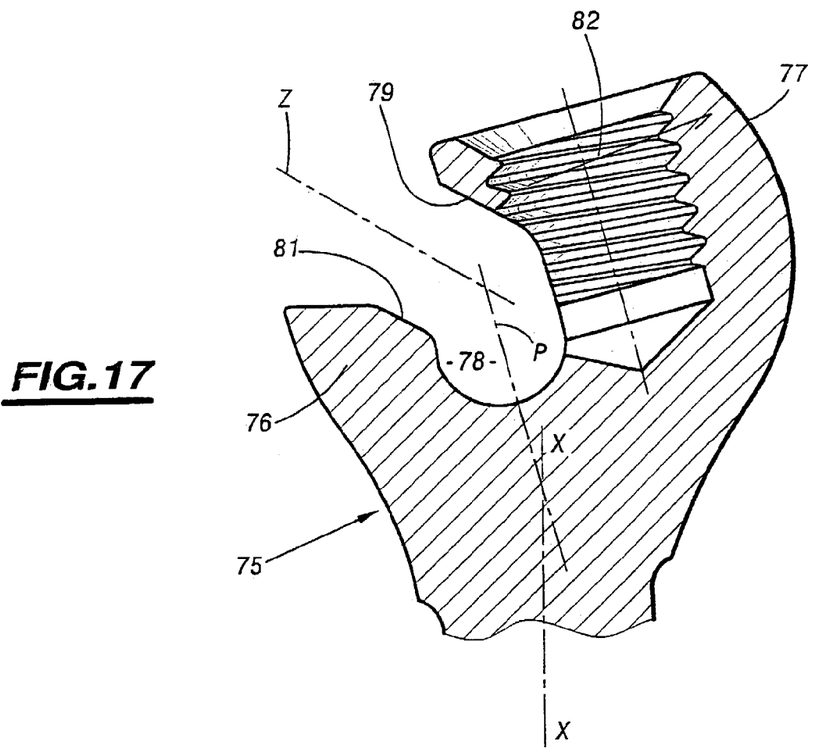
FIG. 17 is a partial section of the screw in FIG. 16.
Figure 18:
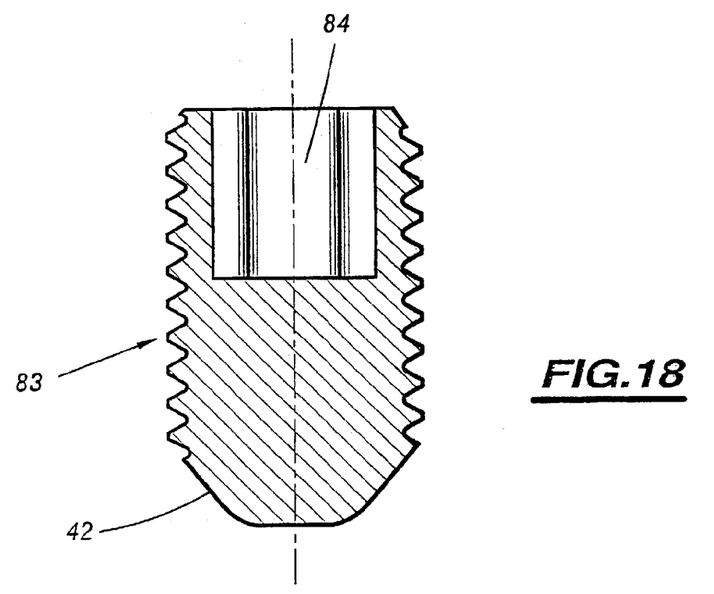
FIG. 18 is a longitudinal section of the means for blocking the screw in FIGS. 16 and 17.

In the third embodiment of the screw 75 shown in FIGS. 16 to 18, the head of the screw 75 consists of a short and fairly thin flank 76 and of a second wider flank 77 which extends beyond the height of the flank 76. These two flanks delimit a channel 78, the bottom of which has an axial plane P at a certain inclination to the longitudinal axis XX of the bone-anchoring member 75, and the end walls 79, 81 of which have an axial plane Z more inclined relative to the axis XX than is the axial plane P.

These walls 79, 81 delimit an entry for the support rod which is thereby guided as far as the bottom of the U-shaped channel 78. Formed in the wide flank 77 there is a threaded hole 82 whose lower truncated part opens into the channel 78 in the zone located between the entry walls 79 and 81

(FIG. 17). In other words, the threaded wall of the hole 82 is interrupted at its part contiguous with the channel 78. The screw 75 is completed by a threaded plug 83 provided with an impression 84 for screwing. The rod 50 having been placed beforehand in the channel 78, the end cone 42 of the plug 83 comes into blocking engagement on the rod 50 (FIG. 16) which is thus blocked in the channel 78 after sufficient screwing. As in the case of the plug 67 in FIG. 13, the upper part of the thread of the plug 83 can be used with a transverse connection plate (not shown) and a locking nut.

In the fourth embodiment illustrated in FIGS. 19 to 22, the screw 85 comprises a channel 86 receiving a support rod 50 and delimited by two flanks 87 and 88. The flank 88 ends in a rectilinear part which is tangent to the cylindrical bottom 86a a of the channel 86. This rectilinear part is continued via a plane surface 89 delimiting a second flank 91, of the screw head, greatly inclined relative to the longitudinal axis XX of the screw 85, in the example shown by about 60°. The bottom 86a is thus connected to a plane surface 88, 89, in which there is a threaded hole 92.

Figure 19:
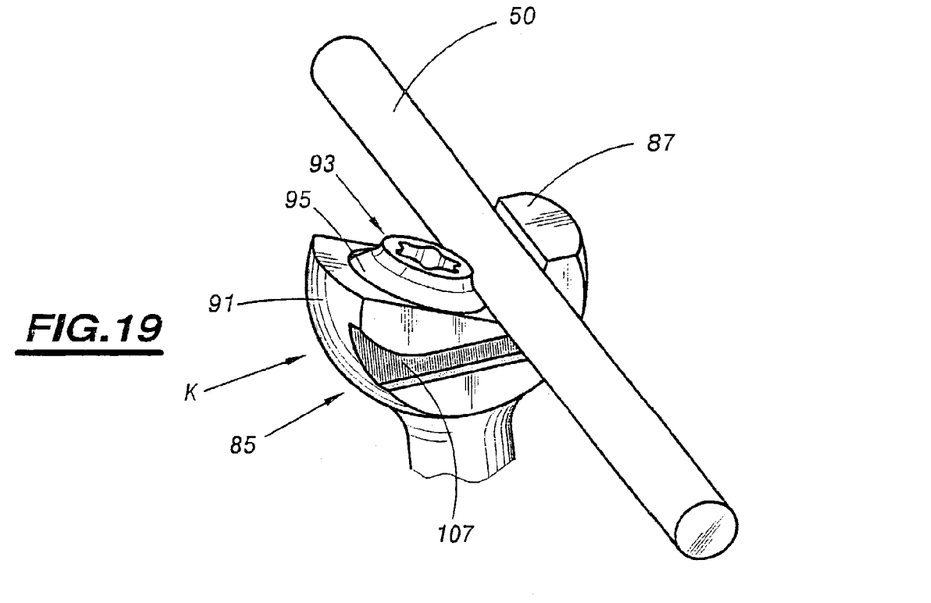
FIG. 19 is a partial perspective view, on an enlarged scale, of a fourth embodiment of the screw in FIGS. 1 to 3 and of its means for blocking the support rod.
Figure 20:
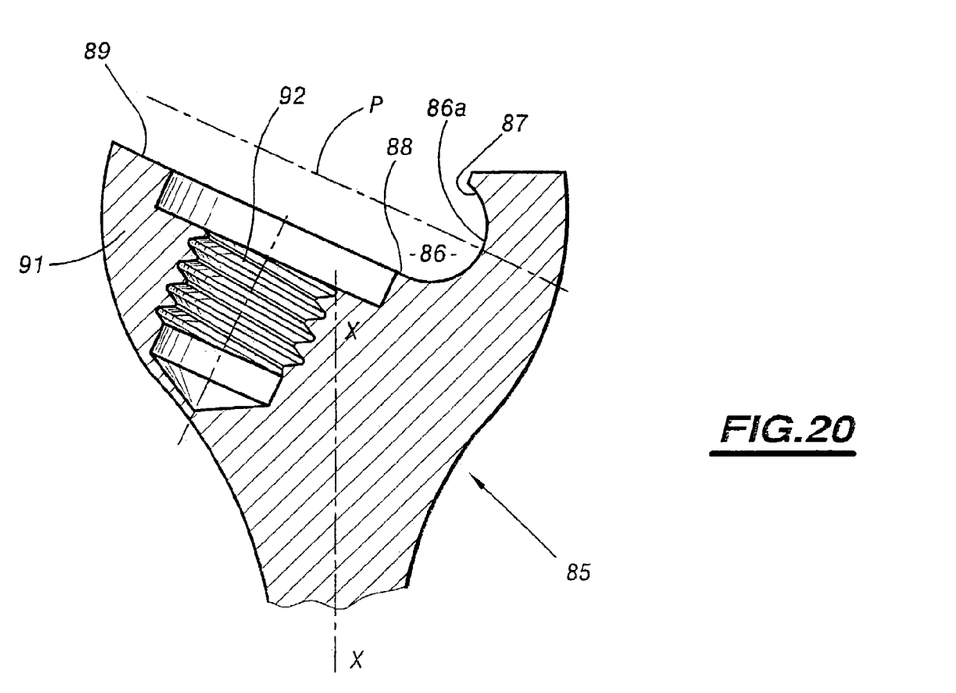
FIG. 20 is a partial section of the screw in FIG. 19.
Figure 21:
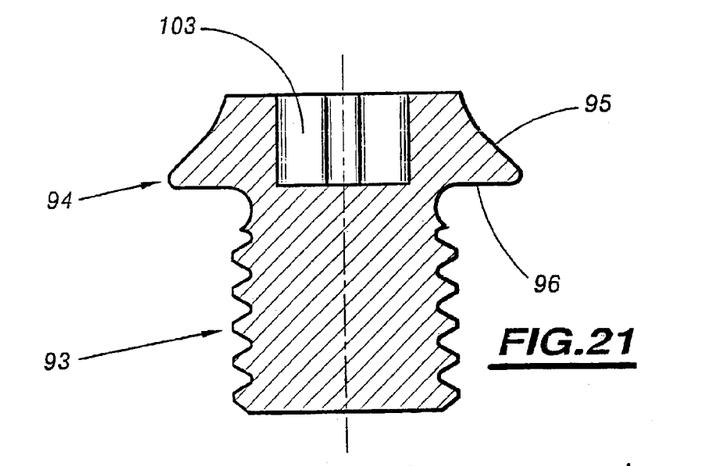
FIG. 21 is a longitudinal section of the blocking means on the screw in FIGS. 19 and 20.
Figures 22, 23:
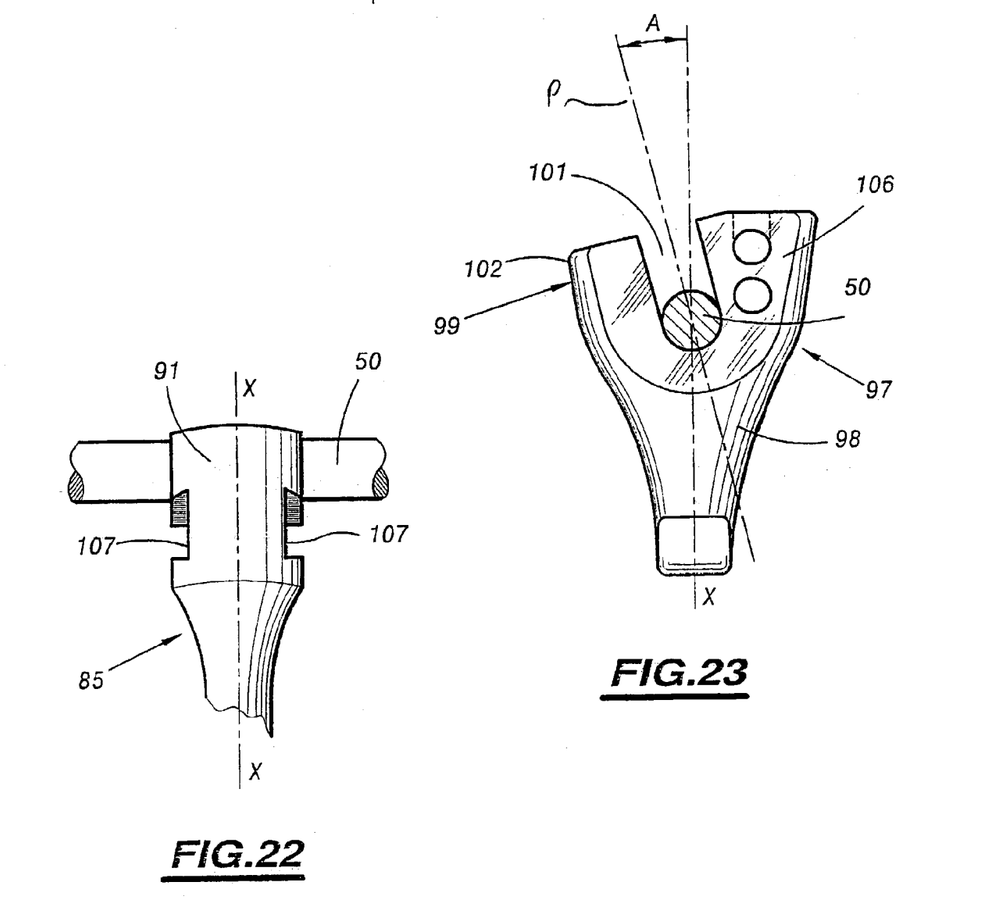
FIG. 22 is a front view of the screw along the arrow K in FIG. 19.
FIG. 23 is a side view of a bone-anchoring hook according to the invention.

Lateral grooves 107 are formed on the sides of the flanks 88, 91 to permit gripping of the screw 85 by an instrument (not shown).

The screw 85 is equipped with a threaded plug 93 preferably with an inverse pitch and equipped with a head 94 consisting of a radially projecting collar. The collar 94 delimits an end span 95 inclined relative to the longitudinal axis of the plug 93 and directed towards the outside of the hole 92 when the plug 93 is screwed into the latter (FIG. 19). The span 95 is connected to a radial surface 96 completing the collar 94. A preliminary insertion of the plug is effected at the works, the plug being delivered pre-assembled on the screw.

To use this embodiment, the surgeon screws the plug 93 into the hole 92, then places the rod 50 in the channel 86. The plug 93 is screwed in by turning it in the opposite direction to the normal direction in the case where its pitch is inverse. After putting the rod 50 into place, the surgeon proceeds to screw the plug 93 in the opposite direction to the previous one, that is to say in the clockwise direction. By this means, the plug 93 begins to emerge from the hole 92 until its span 95 comes to bear on the rod 50 and blocks it against the inner circular wall of the channel 86 (FIG. 19).

The plug 63 can also be provided with a normal pitch, and in this case the rotations of this plug are reversed.

FIG. 23 illustrates a bone-anchoring member 97 consisting of a hook formed by a body 98, having a longitudinal axial plane XX, and a head 99 delimiting a U-shaped channel 101 between two flanks 102 and 106. These latter are provided with an internal threading permitting screwing of a member for blocking the rod 50 in the channel 101. The axial plane P of the channel 101 is inclined relative to the longitudinal axial plane XX of the body 98 by a variable angle A, as in the case of the screw 1 already described. Of course, the same applies to the other screws described above (FIGS. 10-11) which can be replaced in the same way by a hook. In general terms, the arrangement forming the subject of the invention can be used on all types of bone-anchoring hooks: thus, the embodiments in FIGS. 13 to 21 can be used on hooks.

The present application hereby incorporates by reference French Patent Application Number FR 99 16492 filed 24 Dec. 1999 and French Patent Application Number FR 00 06655 filed 3 May 2000 each in their entirety and claims priority to each in accordance with the Paris Convention.

The invention claimed is:

1. An apparatus to support the spine, comprising:
a longitudinal member, said longitudinal member having at least one flat planar face formed therein that extends over at least part of the length of the longitudinal member; and
two bolts, at least one of said bolts including a mounting portion disposed at a first end portion of said bolt and a connector portion disposed at a second end portion of said bolt, said mounting portion having means for engaging a vertebra, said mounting portion having a longitudinal axis, said connector portion having a channel therein that is adapted to receive the longitudinal member, the channel having substantially parallel walls and a longitudinal axial plane, said longitudinal axial plane being substantially parallel to said walls and being oblique to said longitudinal axis of said mounting portion; and a screw having a longitudinal axis and threadably engageable into said connector portion and wherein at least a portion of said screw contacts the longitudinal member when the longitudinal member is placed in the channel of said connector portion, and wherein the channel in said connector portion has a concave bottom with a substantially round cross-section and at least a portion of said longitudinal member has a complementary rounded face to mate with the concave bottom of the channel, and wherein the longitudinal axis of said screw is substantially parallel to the longitudinal axial plane of the channel in said connector portion.

2. The apparatus of claim 1, wherein said screw has a distal end and the distal end is flat to engage the flat planar face of the longitudinal member.

3. The apparatus of claim 1, wherein said mounting portion and said connector portion are integral with each other.

4. The apparatus of claim 1, wherein the longitudinal axial plane is inclined relative to the longitudinal axis of said mounting portion by an angle having a value between zero and 65 degrees.

5. The apparatus of claim 1, wherein the means for engaging a vertebra includes a hook.

6. The apparatus of claim 1, further comprising an instrument attached to at least one of said bolts.

7. The apparatus of claim 6 wherein said instrument is generally tubular and has an angled lower end.

8. An apparatus to support the spine, comprising:
a longitudinal member, said longitudinal member having at least one flat planar face formed therein that extends over at least part of the length of the longitudinal member; and
two bolts, at least one of said bolts including a mounting portion disposed at a first end portion of said bolt and a connector portion disposed at a second end portion of said bolt, said mounting portion having means for engaging a vertebra, said mounting portion having a longitudinal axis, said connector portion having a channel therein that is adapted to receive the longitudinal member, the channel having substantially parallel walls and a longitudinal axial plane, said longitudinal axial plane being substantially parallel to said walls and being oblique to said longitudinal axis of said mounting portion; and a screw having a longitudinal axis and threadably engageable into said connector portion and wherein at least a portion of said screw contacts the longitudinal member when the longitudinal member is placed in the channel of said connector portion, and wherein the channel in said connector portion has a concave bottom with a substantially round cross-section and at least a portion of said longitudinal member has a complementary rounded face to mate with the concave bottom of the channel, wherein said plane and said axis of said mounting portion intersect at a point in said channel.

9. The apparatus of claim 8, wherein said screw has a distal end and the distal end is flat to engage the flat planar face of the longitudinal member.

10. The apparatus of claim 8, wherein said mounting portion and said connector portion are integral with each other.

11. The apparatus of claim 8, wherein the longitudinal axial plane is inclined relative to the longitudinal axis of said mounting portion by an angle having a value between zero and 65 degrees.

12. The apparatus of claim 8, wherein the means for engaging a vertebra includes a hook.

13. The apparatus of claim 8, further comprising an instrument attached to at least one of said bolts.

14. The apparatus of claim 13 wherein said instrument is generally tabular and has an angled lower end.

15. An apparatus to support the spine, comprising:
a longitudinal member, said longitudinal member having at least one flat planar face formed therein that extends over at least part of the length of the longitudinal member; and two bolts, at least one of said bolts including a mounting portion disposed at a first end portion of said bolt and a connector portion disposed at a second end portion of said bolt, said mounting portion having means for engaging a vertebra, said mounting portion having a longitudinal axis, said connector portion having a channel therein that is adapted to receive the longitudinal member, the channel having substantially parallel walls and a longitudinal axial plane, said longitudinal axial plane being substantially parallel to said walls and being oblique to said longitudinal axis of said mounting portion; and a screw having a longitudinal axis and threadably engageable into said connector portion and wherein at least a portion of said screw contacts the longitudinal member when the longitudinal member is placed in the channel of said connector portion, and wherein the channel in said connector portion has a concave bottom with a substantially round cross-section and at least a portion of said longitudinal member has a complementary rounded face to mate with the concave bottom of the channel, wherein the means for engaging a vertebra includes male threads, and said male threads of said bolts have an outside diameter and a core with a core diameter, and wherein the core diameter remains substantially constant between said bolts, while the external diameter of the threads increases from one bolt to the other bolt.

16. The apparatus of claim 15, wherein said screw has a distal end and the distal end is flat to engage the flat planar face of the longitudinal member.

17. The apparatus of claim 15, wherein said mounting portion and said connector portion are integral with each other.

18. The apparatus of claim 15, wherein the longitudinal axial plane is inclined relative to the longitudinal axis of said mounting portion by an angle having a value between zero and 65 degrees.

19. The apparatus of claim 15, wherein the means for engaging a vertebra includes a hook.

20. The apparatus of claim 15, further comprising an instrument attached to at least one of said bolts.

21. The apparatus of claim 20 wherein said instrument is generally tubular and has an angled lower end.

22. An apparatus to support the spine, comprising:
a longitudinal member, said longitudinal member having at least one flat planar face formed therein that extends over at least part of the length of the longitudinal member;
two bolts, at least one of said bolts including a mounting portion disposed at a first end portion of said bolt and a connector portion disposed at a second end portion of said bolt, said mounting portion having means for engaging a vertebra, said mounting portion having a longitudinal axis, said connector portion having a channel therein that is adapted to receive the longitudinal member, the channel having substantially parallel walls and a longitudinal axial plane, said longitudinal axial plane being substantially parallel to said walls and being oblique to said longitudinal axis of said mounting portion; and a screw having a longitudinal axis and threadably engageable into said connector portion and wherein at least a portion of said screw contacts the longitudinal member when the longitudinal member is placed in the channel of said connector portion, and wherein the channel in said connector portion has a concave bottom with a substantially round cross-section and at least a portion of said longitudinal member has a complementary rounded face to mate with the concave bottom of the channel; and
a transverse connection device connecting said bolts.

23. The apparatus of claim 22, wherein said screw has a distal end and the distal end is flat to engage the flat planar face of the longitudinal member.

24. The apparatus of claim 22, wherein said mounting portion and said connector portion are integral with each other.

25. The apparatus of claim 22, wherein the longitudinal axial plane is inclined relative to the longitudinal axis of said mounting portion by an angle having a value between zero and 65 degrees.

26. The apparatus of claim 22, wherein the means for engaging a vertebra includes a hook.

27. The apparatus of claim 22, further comprising an instrument attached to at least one of said bolts.

28. The apparatus of claim 27 wherein said instrument is generally tubular and has an angled lower end.

29. An apparatus to support the spine, comprising:
a longitudinal member, said longitudinal member having at least one flat planar face formed therein that extends over at least part of the length of the longitudinal member; and
two bolts, at least one of said bolts including a mounting portion disposed at a first end portion of said bolt and a connector portion disposed at a second end portion of said bolt, said mounting portion having means for engaging a vertebra, said mounting portion having a longitudinal axis, said connector portion having a channel therein that is adapted to receive the longitudinal member, the channel having substantially parallel walls and a longitudinal axial plane, said longitudinal axial plane being substantially parallel to said walls and being oblique to said longitudinal axis of said mounting portion; and a screw having a longitudinal axis and threadably engageable into said connector portion and wherein at least a portion of said screw contacts the longitudinal member when the longitudinal member is placed in the channel of said connector portion, and wherein the channel in said connector portion has a concave bottom with a substantially round cross-section and at least a portion of said longitudinal member has a complementary rounded face to mate with the concave bottom of the channel, wherein said screw is threadably engaged into said connector portion so that the longitudinal axis of said screw is substantially parallel to the longitudinal axial plane of the channel in said connector portion.

30. The apparatus of claim 29, wherein said screw has a distal end and the distal end is flat to engage the flat planar face of the longitudinal member.

31. The apparatus of claim 29, wherein said mounting portion and said connector portion are integral with each other.

32. The apparatus of claim 29, wherein the longitudinal axial plane is inclined relative to the longitudinal axis of said mounting portion by an angle having a value between zero and 65 degrees.

33. The apparatus of claim 29, wherein the means for engaging a vertebra includes a hook.

34. The apparatus of claim 29, further comprising an instrument attached to at least one of said bolts.

35. The apparatus of claim 34 wherein said instrument is generally tubular and has an angled lower end.

36. An apparatus to support the spine, comprising:

a longitudinal member, said longitudinal member having at least one flat planar face formed therein that extends over at least part of the length of the longitudinal member; and two bolts, at least one of said bolts including a mounting portion disposed at a first end portion of said bolt and a connector portion disposed at a second end portion of said bolt, said mounting portion having means for engaging a vertebra, said mounting portion having a longitudinal axis, said connector portion having a channel therein that is adapted to receive the longitudinal member, the channel having substantially parallel walls and a longitudinal axial plane, said longitudinal axial plane being substantially parallel to said walls and being oblique to said longitudinal axis of said mounting portion; and a screw having a longitudinal axis and threadably engageable into said connector portion and wherein at least a portion of said screw contacts the longitudinal member when the longitudinal member is placed in the channel of said connector portion, and wherein the channel in said connector portion has a concave bottom with a substantially round cross-section and at least a portion of said longitudinal member has a complementary rounded face to mate with the concave bottom of the channel, and wherein said mounting portion and said connector portion are monolithic with each other.

* * * * *